US010039992B2

(12) United States Patent
Rivera

(10) Patent No.: US 10,039,992 B2
(45) Date of Patent: Aug. 7, 2018

(54) METHODS AND APPARATUS FOR CONCEALING MEDICAL EQUIPMENT

(71) Applicant: Anilu's Partners, Inc., Scottsdale, AZ (US)

(72) Inventor: Alma Rivera, Scottsdale, AZ (US)

(73) Assignee: Anilu's Partners, Inc., Scottsdale, AZ (US)

( * ) Notice: Subject to any disclaimer, the term of this patent is extended or adjusted under 35 U.S.C. 154(b) by 0 days.

(21) Appl. No.: 15/132,216

(22) Filed: Apr. 18, 2016

(65) Prior Publication Data

US 2017/0296939 A1 Oct. 19, 2017

Related U.S. Application Data

(60) Provisional application No. 62/149,497, filed on Apr. 17, 2015.

(51) Int. Cl.
*A61M 5/14* (2006.01)
*A63H 33/00* (2006.01)
*A63H 33/16* (2006.01)
*A61J 1/14* (2006.01)

(52) U.S. Cl.
CPC ............ *A63H 33/16* (2013.01); *A61J 1/1462* (2013.01); *A61M 5/14* (2013.01); *A61M 2205/59* (2013.01)

(58) Field of Classification Search
CPC ............ A61M 2205/59; A61M 5/1415; A61B 5/6896; A61C 2203/00; A61J 1/1462
USPC .................. 446/71, 72, 77, 73, 74; 604/408
See application file for complete search history.

(56) References Cited

U.S. PATENT DOCUMENTS

| | | | | |
|---|---|---|---|---|
| 5,044,378 A | * | 9/1991 | Toma | A61M 5/52 128/898 |
| 5,078,640 A | * | 1/1992 | Berman | A63H 3/003 135/73 |
| 5,295,964 A | * | 3/1994 | Gauthier | A61J 1/1462 604/113 |
| 5,605,485 A | * | 2/1997 | Spector | A63H 3/003 222/78 |
| 6,165,035 A | * | 12/2000 | Avner | A61B 1/227 446/369 |
| D442,278 S | * | 5/2001 | Rury | A61M 5/14 D24/118 |
| 6,322,539 B1 | * | 11/2001 | Cook | A61M 25/02 604/174 |
| 6,520,639 B2 | * | 2/2003 | Avner | A61B 1/227 351/205 |

(Continued)

*Primary Examiner* — Alexander Niconovich
(74) *Attorney, Agent, or Firm* — The Noblitt Group, PLLC

(57) ABSTRACT

Various embodiments of the present technology provide structures for a cover for obscuring medical equipment and methods of making the same. The cover may extend over the medical equipment and comprise a plurality of peripheral flaps that extend over the sides of the medical equipment to conceal at least a portion of the medical equipment. In one embodiment, the cover may comprise a central member configured to extend over the top of the medical equipment. The cover may comprise one or more peripheral flaps extending out from the central member and configured to overlay and conceal a portion of the medical equipment and/or accessories attached to the medical equipment. In some embodiments, the cover may comprise spaces between the peripheral flaps provide access to the medical equipment.

20 Claims, 7 Drawing Sheets

(56) References Cited

U.S. PATENT DOCUMENTS

Figure 1B:
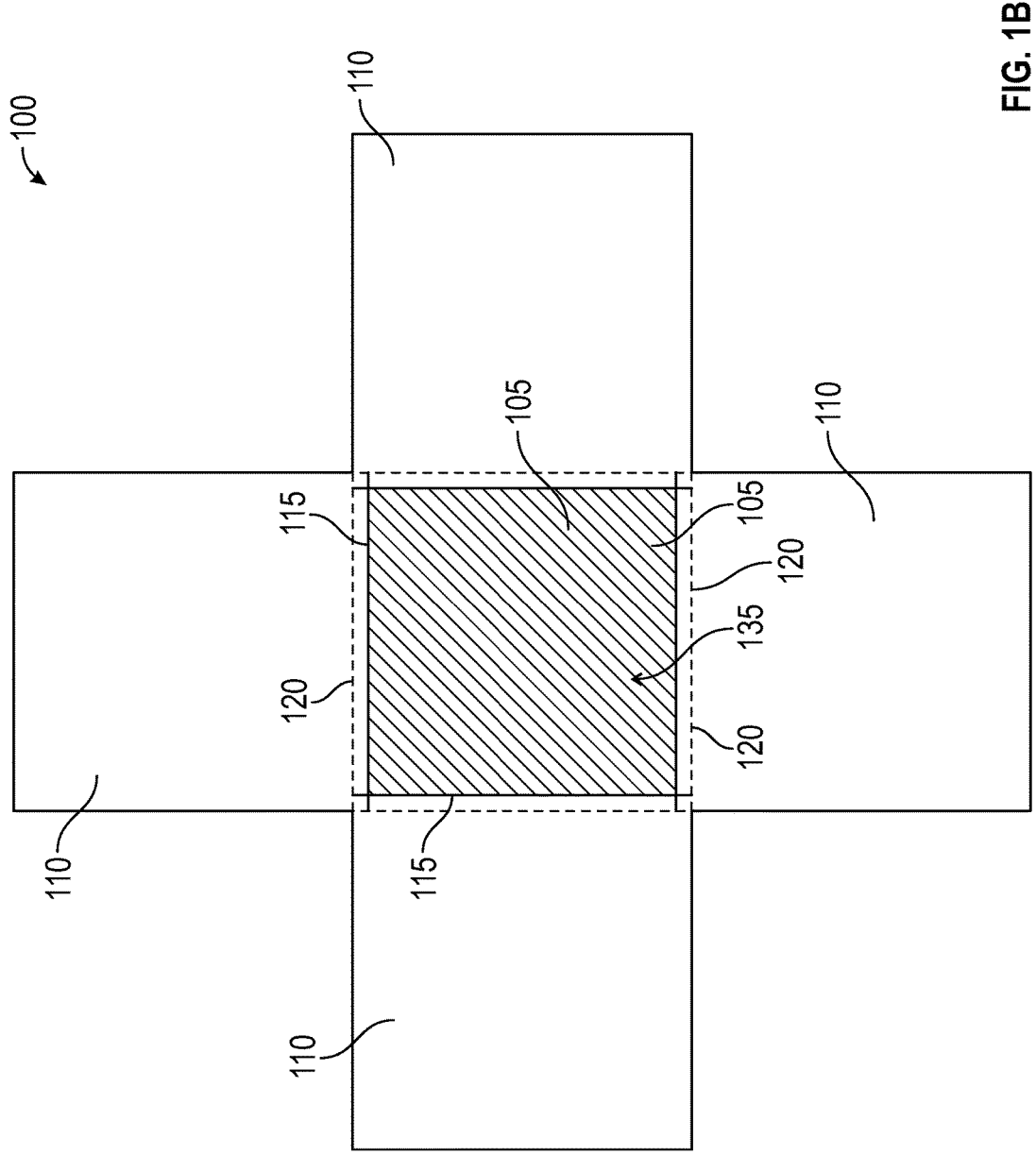

| | | | | |
|---|---|---|---|---|
| 6,540,724 | B1* | 4/2003 | Harris | A61M 25/02 |
| | | | | 604/174 |
| 6,613,036 | B1* | 9/2003 | Farmer | A61J 1/10 |
| | | | | 206/438 |
| 6,746,440 | B2* | 6/2004 | Magnusson | A61M 5/445 |
| | | | | 604/113 |
| 7,556,226 | B2* | 7/2009 | Muncie | A61M 5/1415 |
| | | | | 248/176.1 |
| 2001/0001188 | A1* | 5/2001 | Avner | A61B 1/227 |
| | | | | 181/126 |
| 2004/0077998 | A1* | 4/2004 | Morris | A61M 5/14 |
| | | | | 604/93.01 |
| 2004/0205875 | A1* | 10/2004 | Byrne | A41D 13/08 |
| | | | | 2/16 |
| 2006/0089077 | A1* | 4/2006 | Wittschen | A61J 7/0053 |
| | | | | 446/77 |
| 2006/0272651 | A1* | 12/2006 | Ortel | A61B 46/00 |
| | | | | 128/869 |
| 2008/0096459 | A1* | 4/2008 | Mingle | A61J 1/1462 |
| | | | | 446/74 |
| 2008/0139076 | A1* | 6/2008 | Frasier-Scott | A61J 1/1462 |
| | | | | 446/72 |
| 2010/0243834 | A1* | 9/2010 | Salser | A61M 5/1415 |
| | | | | 248/219.4 |
| 2010/0274214 | A1* | 10/2010 | Frasier-Scott | A61J 1/1462 |
| | | | | 604/408 |
| 2012/0157758 | A1* | 6/2012 | Dietz | A61M 21/02 |
| | | | | 600/28 |

* cited by examiner

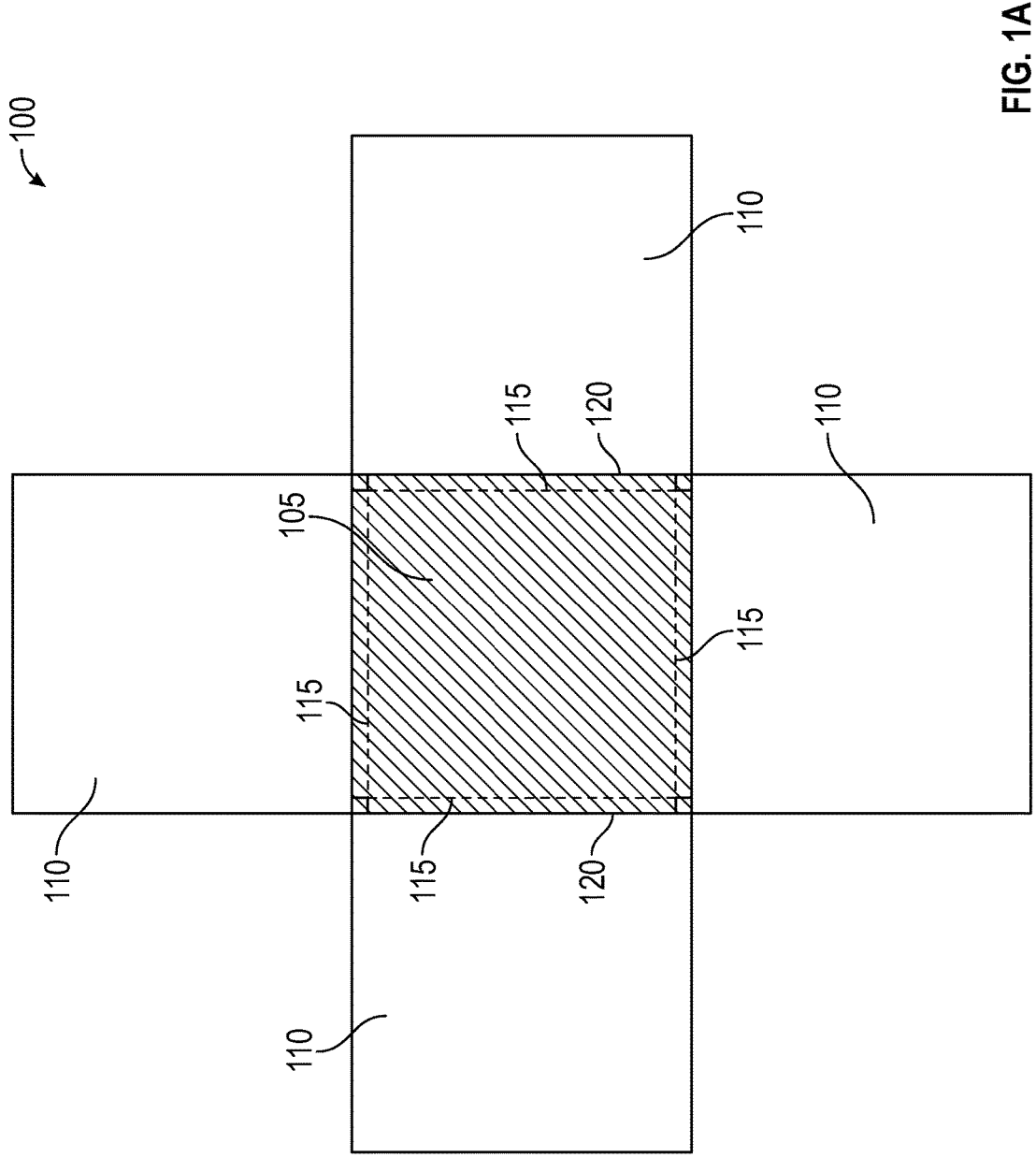

METHODS AND APPARATUS FOR CONCEALING MEDICAL EQUIPMENT

CROSS-REFERENCES TO RELATED APPLICATIONS

This application claims priority to U.S. Provisional Patent Application Ser. No. 62/149,497, filed on Apr. 17, 2015, and incorporates the disclosure of that application by reference. To the extent that the present disclosure conflicts with the referenced application, however, the present disclosure is to be given priority.

BACKGROUND

Medical equipment used at a patient's bedside may cause the patient distress for a variety of reasons. Medical equipment may have bright lights that affect the patient's ability to rest and sleep. Medical equipment may also have complicated appearing components that are intimidating for patients, further adding to the patient's anxiety.

Medical equipment may be particularly daunting for patients that are children. The clinical appearance of indicator lights, IV fluid bags, tubes and the like may be frightening to children. Clinical settings that treat children have gone to great lengths to make the environment less stressful to improve patient cooperation, treatment tolerance, and recuperation. Clinical settings such as doctor's offices, hospital rooms, and treatment rooms may employ paint, murals, decorations, and toys to improve the experience for the child and help them cope with treatment. However, the medical equipment itself such as monitors, hospital beds, gas supply devices, and the like remain an intimidating and stress-inducing necessity in medical settings.

SUMMARY

Various embodiments of the present technology provide structures for a cover for obscuring medical equipment and methods of making the same. The cover may extend over the medical equipment and comprise a plurality of peripheral flaps that extend over the sides of the medical equipment to conceal at least a portion of the medical equipment. In one embodiment, the cover may comprise a central member configured to extend over the top of the medical equipment. The cover may comprise one or more peripheral flaps extending out from the central member and configured to overlay and conceal a portion of the medical equipment and/or accessories attached to the medical equipment. In some embodiments, the cover may comprise spaces between the peripheral flaps provide access to the medical equipment.

BRIEF DESCRIPTION OF THE DRAWING FIGURES

A more complete understanding of the present invention may be derived by referring to the detailed description when considered in connection with the following illustrative figures. In the following figures, like reference numbers refer to similar elements and steps throughout the figures.

Elements and steps in the figures are illustrated for simplicity and clarity and have not necessarily been rendered according to any particular sequence or scale. For example, steps that may be performed concurrently or in different order are illustrated in the figures to help to improve understanding of embodiments of the present invention.

Figure 2:
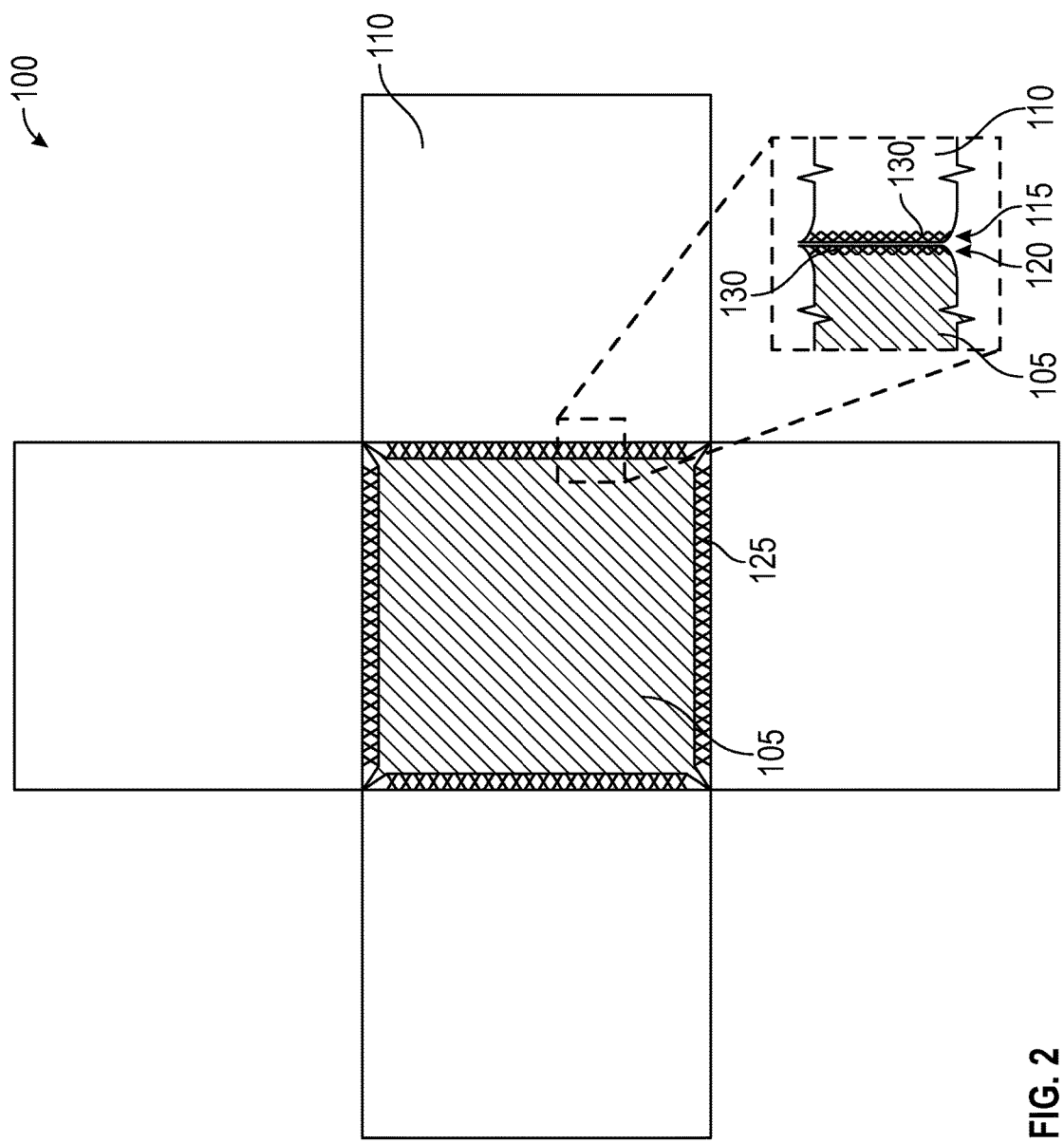
Figure 3:
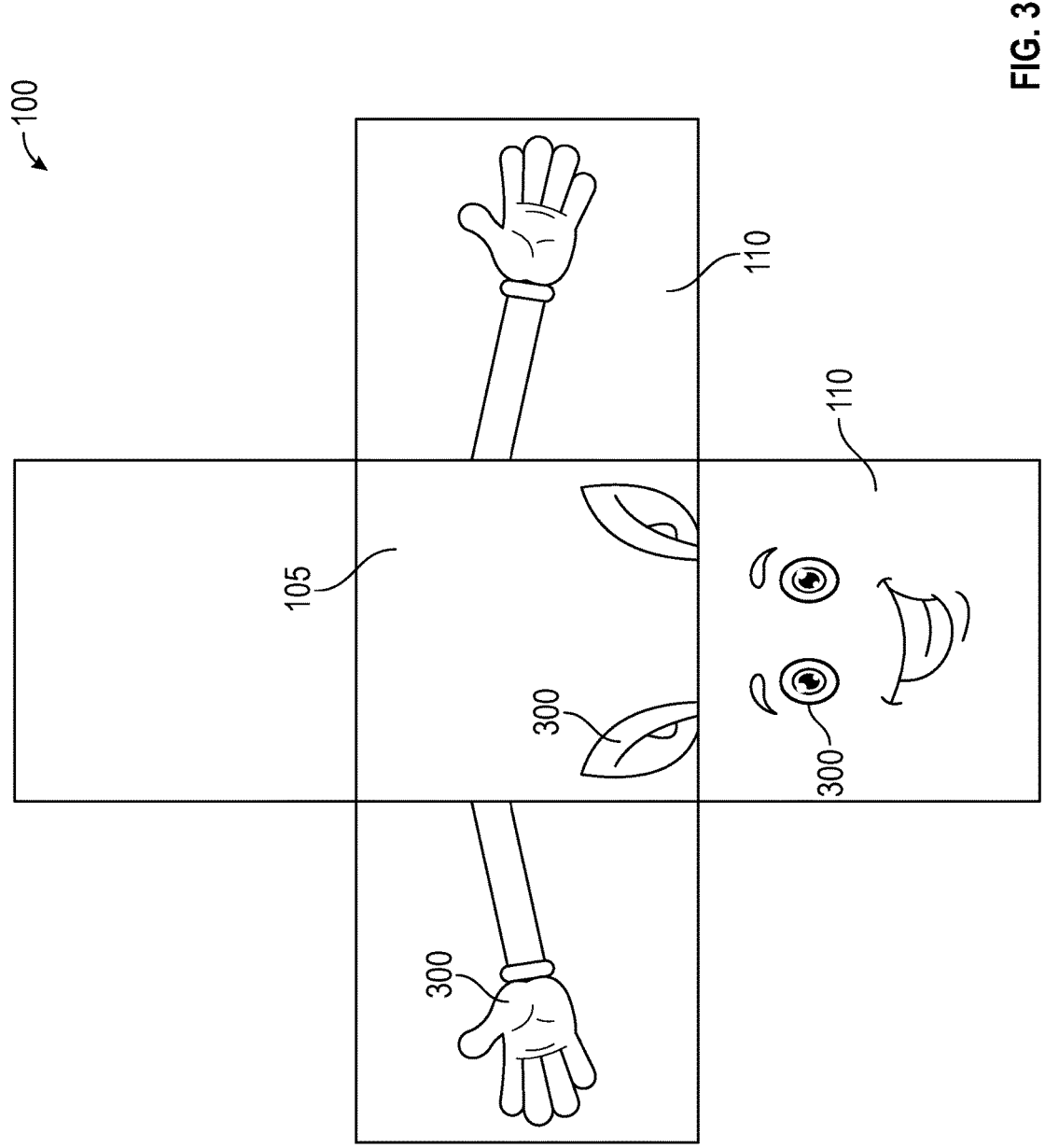
Figure 4:
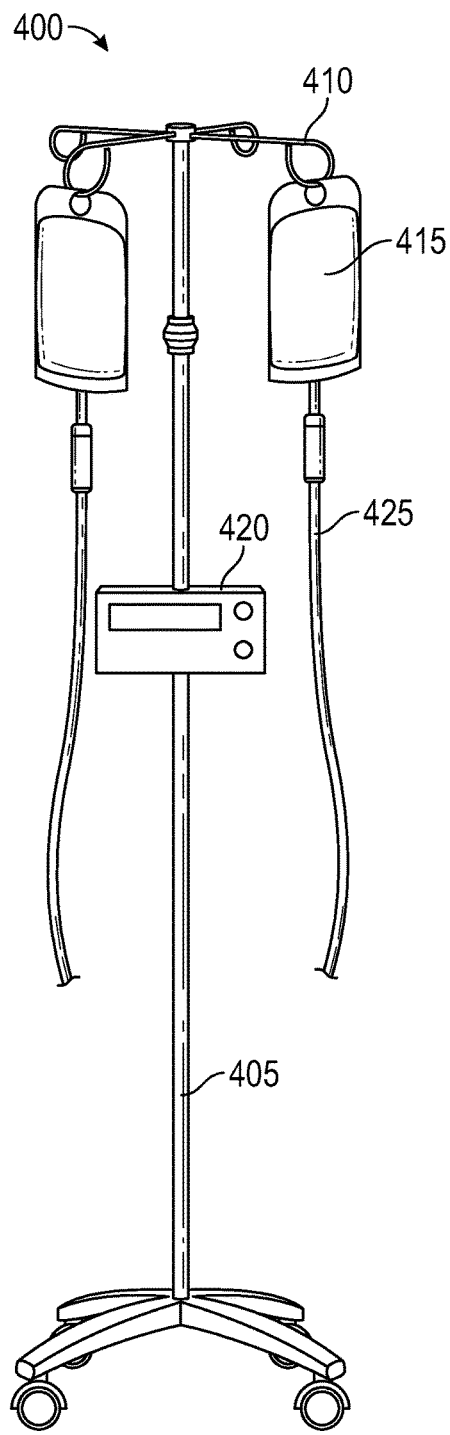
Figure 5:
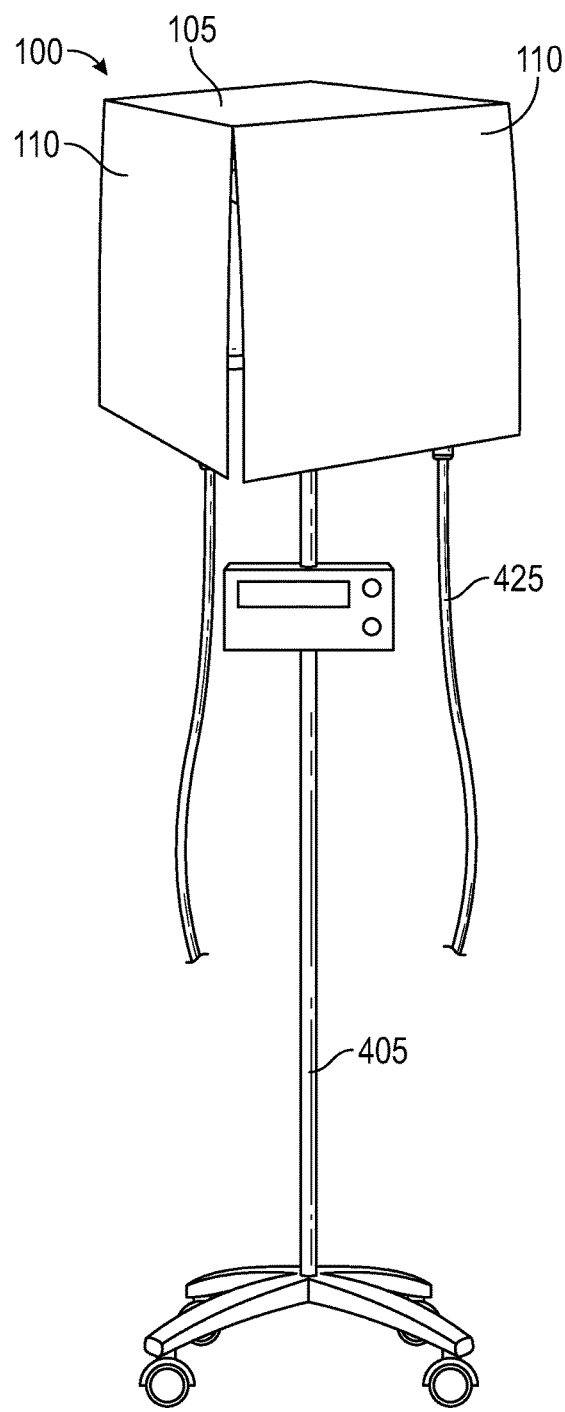
Figure 6:
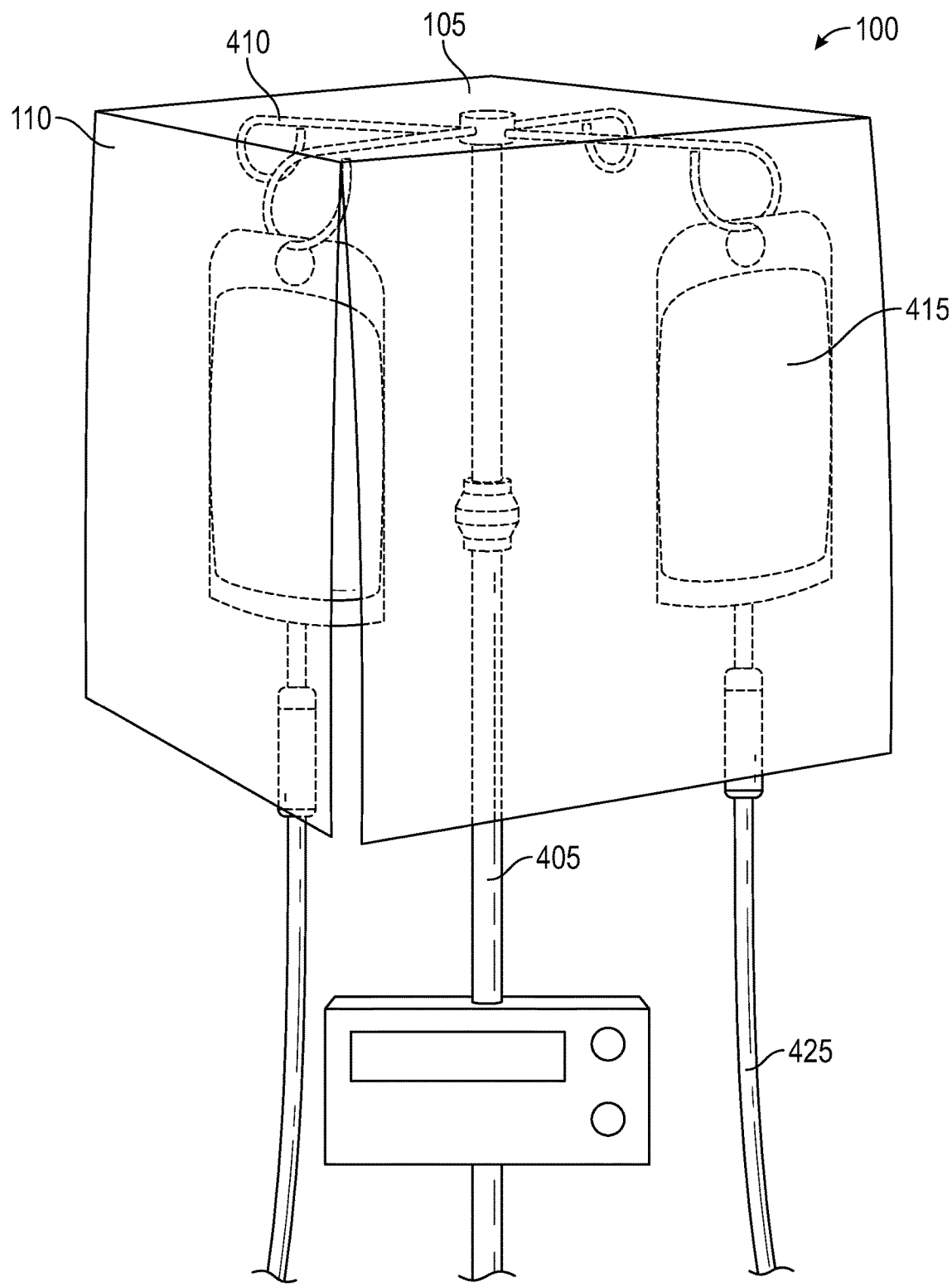
Figure 7:
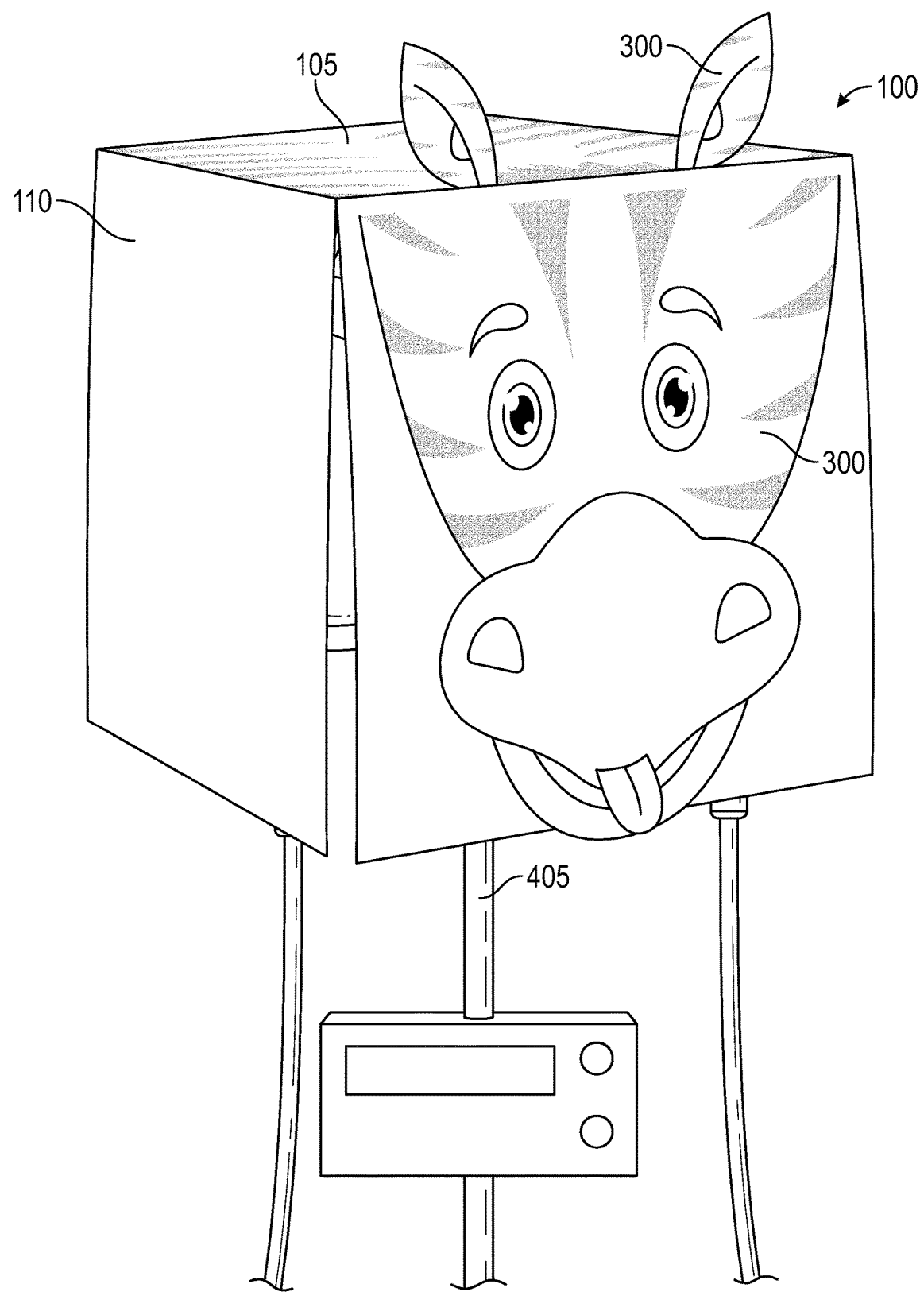

The figures described are for illustration purposes only and are not intended to limit the scope of the present disclosure in any way. Various aspects of the present invention may be more fully understood from the detailed description and the accompanying drawing figures, wherein:

FIGS. 1A-B representatively illustrates a top and bottom view of an exemplary medical equipment cover;

FIG. 2 representatively illustrates sewn seams of the exemplary medical equipment cover;

FIG. 3 representatively illustrates a top view of the exemplary medical equipment cover comprising a decoration;

FIG. 4 representatively illustrates prior art medical equipment comprising an IV pole and accessories;

FIG. 5 representatively illustrates the exemplary medical equipment cover overlaying an IV pole;

FIG. 6 representatively illustrates the exemplary medical equipment cover overlaying an IV pole;

FIG. 7 representatively illustrates the exemplary medical equipment cover comprising a decoration and overlaying an IV pole; and FIG. 8 illustrates an exemplary method of making the medical equipment cover.

DETAILED DESCRIPTION OF EXEMPLARY EMBODIMENTS

The present technology may be described in terms of functional block components and various processing steps. Such functional blocks may be realized by any number of components configured to perform the specified functions and achieve the various results. For example, the present technology may employ various types of materials, fasteners, and/or adhesives for manufacturing a medical equipment cover. In addition, the present technology may be practiced in conjunction with any conventional medical equipment for humans and/or animals, and the system described is merely one exemplary application for the technology.

Methods and apparatus for a medical equipment cover according to various aspects of the present technology may operate in conjunction with any suitable equipment that may be found in a hospital room such as intravenous poles (IV pole or IV stand), dialysis machines, monitors, other electrical equipment, wheelchairs, and/or hospital beds. Various representative implementations of the present technology may be applied to any medical equipment for concealing the medical equipment from a patient's view.

Referring to FIGS. 1-7, some embodiments of a medical equipment cover 100 may be configured to cover an IV pole 400. However, the medical equipment cover 100 may be configured to cover any medical equipment. As shown in FIG. 4, various types of IV poles 400 may have multiple accessories attached to a pole 405 or to a hook assembly 410. For example, the accessories may comprise an IV fluid bag 415 having a tube 425 extending downwardly therefrom. The fluid bag 415 may hang from a hook (not shown) on the hook assembly 410 to deliver a therapy to the patient. The accessories may also comprise electronic equipment 420, such as IV infusion pumps, enteral feeding pumps, patient monitors, intravenous drip feed monitors and the like. The accessories attached to the IV pole 400 may be intimidating or traumatizing, causing fear or discomfort to a patient that requires connection to the fluid bags 415 on the IV pole 400 for delivery of a therapy, particularly where the patient is a child. The accessories may also emit light, disrupting the patient's ability to rest and sleep. As shown in FIGS. 5 and 6, the cover 100 may at least partially obscure and/or conceal one or more accessories attached to the IV pole 400 from view.

Referring to FIGS. 1A-B, an exemplary embodiment of the medical equipment cover 100 is shown. The cover 100 may comprise a generally square central member 105 that may be coupled to a plurality of peripheral flaps 110. Each of the peripheral flaps 110 may be coupled to an outer edge element of the central member 105 and may extends downwardly therefrom to form an internal volume configured to cover the medical equipment. For example, the inner volume may be occupied by the hook assembly 410 and the IV fluid bags 415, if present. In various embodiments, the peripheral flaps 110 may not be coupled to each other or may be removably attached to each other such that edges of adjacent peripheral flaps 110 are not coupled to provide access to the medical equipment without removal of the cover 100. In various embodiments, the edges of adjacent peripheral flaps 110 may be proximate to one another and uncoupled to provide access to the medical equipment without removal of the cover and the peripheral flaps 110 may be configured to overlay and obscure the portion of the medical equipment.

The peripheral flaps 110 may be coupled to the central member 105 by any suitable method or device such as a sewn seam, adhesive, clips, staples, a hook and loop fastener, tape, zipper, buttons, and the like. As shown in the top view of FIG. 1A, an inner edge 115 of each peripheral flap 110 may be positioned underneath each outer edge 120 of the central member 105. Accordingly, as shown in the bottom view of FIG. 1B, the inner edge 115 of each peripheral flap 110 may lay over a bottom face 135 of the central member 105. Any suitable faster may be applied to the area of overlap between each peripheral flap 110 and the central member 105.

In another embodiment, as shown in FIG. 2, a top face of the inner edge 115 of each peripheral flap 110 may contact the top face of each edge 120 of the central member 105 and fastened with a sewn seam 130. In this embodiment, all raw edges of material will be hidden from the top view of the cover 100. Various embodiments may employ a piece of material, such as batting, to cover the bottom face of the cover 100 to seal raw edges of material that have been fastened.

The cover 100 may be constructed from any suitable material such as fabric, felt, plastic, cloth, paper, leather, batting, and the like. In some embodiments, the material may be at least partially to completely opaque to conceal the medical equipment it covers. The peripheral flaps 110 may or may not be made of the same material as the central member 105. In various embodiments, the material for the central member 105 and/or the peripheral flaps 110 may be selected according to any suitable criteria such as rigidity or firmness to overlay the medical equipment, allergenicity, opacity, washability for sanitary purposes, and/or flexibility to roll, fold, or tuck the peripheral flap 110 to allow access to the accessories, such as to change an IV fluid bag 415. The flexibility of the material may prevent the need to remove the cover 100 from the IV pole 400 or the medical equipment while accessing the accessories.

Various embodiments of the cover 100 may further comprise a surface treatment configured to adorn at least one outside surface of the central member 105 and/or the peripheral flaps 110. The surface treatment may comprise any suitable design, element, embellishment, or the like configured to add an aesthetic element to the cover 100. Referring to FIG. 3, in one embodiment, the surface treatment may comprise a decoration 300 presented as a smiling face disposed on an exterior facing surface of a first peripheral flap 110 to face the patient. The decoration 300 may include additional elements such as ears and hands disposed on an exterior facing surface of additional peripheral flaps 110. In an alternative embodiment, referring now to FIG. 7, the decoration 300 may comprise an animal likeness such as a zebra face suitably configured to cover the IV pole 405 and conceal the hook assembly 410 and IV fluid bags 415 (as shown in FIG. 6). The cover 100 may conceal the desired accessories of the medical equipment with or without such decorations 300. However, the decorations 300 may provide further distraction for the patient away from the medical equipment to diminish patient distress.

In various embodiments, the decorations 300 may comprise any decorative features such as letters, names, symbols, artwork such as the likeness of animals. In some embodiments, the decorations 300 may be coupled to the central member 105 and/or the peripheral flaps 110 with any suitable permanent or removable fastener, such as with the hook and loop fastener. The feature of removability of the decorative features may allow the patient to selectively modify the decorations 300. For example, the decoration 300 may be configured to allow the patient to turn the mouth of the face shown in FIG. 3 up for a happy face or down for a sad face to communicate how the patient is feeling without having to speak.

The medical equipment cover 100 may have any suitable size dimensions for covering the medical equipment. In various embodiments, the peripheral flaps 110 and the central member 105 may be the same size or a different size. In some embodiments, the plurality of the peripheral flaps 110 may be the same size. In other embodiments, each of the peripheral flaps 110 may be a different size than other peripheral flaps 110. In various embodiments, the dimensions of the central piece 105 may be any dimensions that are adequate to cover the top of the medical equipment. For example, to rest on top of a conventional IV pole (as shown in FIGS. 5-7), the central member 105 may comprise generally a square shape of about 9 inches by about 9 inches or a rectangular shape of about 9 inches by about 12 inches. Similarly, in various embodiments, the peripheral flaps 110 may comprise a generally square shape of about 9 inches by about 9 inches or a rectangular shape of about 9 inches by about 12 inches. In some embodiments, the central member 105 and the peripheral flaps 110 may comprise an amorphous shape to create a cover 100 that is not box-shaped.

An exemplary method of making the medical equipment cover 100 of the present technology as applied to an IV pole is shown in FIG. 8 (800). The portions of the IV pole to be covered may be measured (805). For example, the dimensions of the hook assembly and the drop length from the top of the hook assembly to the bottom of the accessory to be covered may be measured. A substantially opaque material may be cut according to the dimensions of the hook assembly to create a central member (810). Another piece of the material may be cut according to the dimensions of the drop length from the top of the hook assembly to the bottom of the accessory, or a portion thereof if covering the entire accessory is not desirable, to create one or more peripheral flaps (815). For example, one embodiment of the cover 100 created for an IV pole may have three peripheral flaps to cover IV bags and/or other accessories attached to the pole on the side facing the patient. In another embodiment, the cover 100 created for an IV pole may have four peripheral flaps for covering all sides of the IV pole. The one or more peripheral flaps may be coupled to the central member with any suitable fastener, such as sewn seams and/or an non allergenic adhesive (820). Decorations may be affixed to the central member and/or the one or more peripheral flaps to draw the patient's attention away from the IV pole and onto a visually appealing decorative application, such as funny face or animal (825).

In the foregoing description, the technology has been described with reference to specific exemplary embodiments. Various modifications and changes may be made, however, without departing from the scope of the present invention as set forth. The description and figures are to be regarded in an illustrative manner, rather than a restrictive one and all such modifications are intended to be included within the scope of the present invention. Accordingly, the scope of the technology should be determined by the generic embodiments described and their legal equivalents rather than by merely the specific examples described above. For example, the steps recited in any method or process embodiment may be executed in any appropriate order and are not limited to the explicit order presented in the specific examples. Additionally, the components and/or elements recited in any system embodiment may be combined in a variety of permutations to produce substantially the same result as the present invention and are accordingly not limited to the specific configuration recited in the specific examples.

Benefits, other advantages and solutions to problems have been described above with regard to particular embodiments. Any benefit, advantage, solution to problems or any element that may cause any particular benefit, advantage or solution to occur or to become more pronounced, however, is not to be construed as a critical, required or essential feature or component.

The terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

What is claimed is:

1. A system for covering at least a portion of a medical equipment comprising:
    a central member having a plurality of outer edge elements; and
    a plurality of peripheral flaps, wherein each of the plurality of peripheral flaps is coupled to an outer edge element of the central member and extending downwardly therefrom to form an internal volume configured to cover the medical equipment, wherein:
        the central member is configured to extend over a top portion of the medical equipment; and
        adjacent peripheral flaps are proximate to one another and uncoupled from each other to provide access to the medical equipment without removal of the system and the peripheral flaps are configured to overlay and obscure the portion of the medical equipment.

2. The system of claim 1, wherein the peripheral flaps are dimensioned to cover at least a portion of the medical equipment.

3. The system of claim 1, wherein the central member is about 9 inches by about 9 inches and each of the plurality of the peripheral flaps are about 9 inches by about 12 inches.

4. The system of claim 1, wherein the peripheral flaps comprise an opaque material.

5. The system of claim 1, wherein the peripheral flaps are coupled to the central member with a sewn seam.

6. The system of claim 1, wherein the peripheral flaps are coupled to the central member with an adhesive.

7. The system of claim 1, wherein the cover comprises four peripheral flaps, wherein each peripheral flap:
    is at least one of a square and a rectangular shape; and
    extends from an edge of the central member.

8. The system of claim 1, further comprising a decoration coupled to an exterior facing surface of at least one of the central member and the peripheral flaps.

9. The system of claim 8, wherein the decoration is removably coupled to the exterior facing surface of the at least one of the central member and the peripheral flaps.

10. A system for covering at least a portion of an IV pole comprising a pole for coupling an accessory and a hook assembly for attaching an IV bag, the system comprising:
    a central member having a plurality of outer edge elements;
    a plurality of peripheral flaps, wherein each of the plurality of peripheral flaps is coupled to an outer edge element of the central member with at least one of a sewn seam and an adhesive and extending downwardly therefrom to form an internal volume configured to cover the hook assembly and the accessory, wherein:
        the central member is configured to extend over a top portion of the IV pole; and
        adjacent peripheral flaps are proximate to one another and uncoupled from each other to provide access to the IV pole without removal of the system and the peripheral flaps are configured to overlay and obscure the hook assembly and the accessory; and
    a decoration coupled to an exterior facing surface of at least one of the central member and the peripheral flaps.

11. The system of claim 10, wherein the decoration is removably coupled to the exterior facing surface of the at least one of the central member and the peripheral flaps.

12. The system of claim 10, wherein the central member is a square shape dimensioned to extend to an edge of the hook assembly.

13. The system of claim 10, wherein the cover comprises four peripheral flaps, wherein each peripheral flap:
    is at least one of a square shape and a rectangular shape; and
    extends from an edge of the central member.

14. The system of claim 10, wherein the central member is about 9 inches by about 9 inches and each of the plurality of the peripheral flap is about 9 inches by about 12 inches to cover the IV bag.

15. The system of claim 10, wherein at least one of the central member and the plurality of peripheral flaps comprise an opaque material.

16. A method of making a cover for an IV pole having a pole for coupling an accessory and a hook assembly for attaching an IV bag, the method comprising:
    creating a central member having a plurality of outer edge elements by forming a first opaque material to dimensions suitable to cover the hook assembly;

creating a plurality of peripheral flaps by forming a second opaque material to dimensions suitable to extend from the central member to at least partially cover at least one of the IV bag and the accessory; and coupling each of the plurality of peripheral flaps to an outer edge element of the central member, wherein adjacent peripheral flaps are proximate to one another and uncoupled from each other to provide access to the at least one of the IV bag and the accessory without removal of the cover.

17. The method of claim 16, further comprising coupling decorations to an outside face of at least one of the central member and the plurality of peripheral flaps.

18. The method of claim 16, wherein the plurality of peripheral flaps are coupled to the central member by a sewn seam.

19. The method of claim 16, wherein the plurality of peripheral flaps are coupled to the central member by an adhesive.

20. The system of claim 16, wherein the central member is about 9 inches by about 9 inches and each of the plurality of peripheral flaps are about 9 inches by about 12 inches to cover the IV bag.

\* \* \* \* \*